(12) United States Patent
Zaret et al.

(10) Patent No.: US 8,329,467 B2
(45) Date of Patent: Dec. 11, 2012

(54) COMPOSITIONS AND METHODS FOR ALTERING PANCREAS OR LIVER FUNCTION

(75) Inventors: Kenneth S. Zaret, Elkins Park, PA (US); Yasushige Kashima, Oyama (JP)

(73) Assignee: Fox Chase Cancer Center, Philadelphia, PA (US)

( * ) Notice: Subject to any disclaimer, the term of this patent is extended or adjusted under 35 U.S.C. 154(b) by 379 days.

(21) Appl. No.: 12/598,437

(22) PCT Filed: Apr. 18, 2008

(86) PCT No.: PCT/US2008/060726
§ 371 (c)(1),
(2), (4) Date: Nov. 2, 2009

(87) PCT Pub. No.: WO2008/137280
PCT Pub. Date: Nov. 13, 2008

(65) Prior Publication Data
US 2010/0129351 A1 May 27, 2010

Related U.S. Application Data

(60) Provisional application No. 60/915,727, filed on May 3, 2007.

(51) Int. Cl.
*C12N 5/00* (2006.01)
(52) U.S. Cl. ............ 435/377; 435/325; 514/16.5
(58) Field of Classification Search .................. None
See application file for complete search history.

(56) References Cited

U.S. PATENT DOCUMENTS

| | | | |
|---|---|---|---|
| 4,353,888 A | 10/1982 | Sefton | 424/25 |
| 4,391,909 A | 7/1983 | Lim | 435/178 |
| 4,892,538 A | 1/1990 | Aebischer et al. | 604/891.1 |
| 5,106,627 A | 4/1992 | Aebischer et al. | 424/424 |
| 2002/0025308 A1* | 2/2002 | Costantino et al. | 424/93.21 |
| 2003/0207347 A1 | 11/2003 | Olson et al. | 435/69.1 |
| 2004/0110289 A1* | 6/2004 | Ludlow et al. | 435/370 |
| 2004/0248178 A1 | 12/2004 | Olson et al. | 435/6 |
| 2006/0019896 A1 | 1/2006 | Li et al. | 514/12 |
| 2006/0025335 A1 | 2/2006 | Kinane et al. | 514/12 |

OTHER PUBLICATIONS

Aebischer et al. "Transplantation of Polymer Encapsulated Neurotransmitter Secreting Cells: Effect of the Encapsulation Technique" Journal of Biomechanical Engineering 1991 vol. 113: 178-183.
Carmeliet, P. and Tessier-Lavigne, M. "Common Mechanisms of Nerve and Blood Vessel Wiring" Nature 2005 vol. 436: 193-200.
Chen et al. "Instant Hepatic Differentiation of Human Embryonic Stem Cells Using Activin A and a Deleted Variant of HGF" Cell Transplantation 2006 vol. 15: 865-871.
Chiang, M. and Melton, D.A. "Single-Cell Transcript Analysis of Pancreas Development" Developmental Cell 2003 vol. 4: 383-393.
Cleaver, O. And Melton, D.A. "Endothelial Signaling During Development" Nature Medicine 2003 vol. 9(6): 661-668.
Guthrie, S. "Axon Guidance: Netrin Receptors are Revealed" Current Biology 1997 vol. 7: R6-R9.
Hoffman et al. "NGF Released from a Polymer Matrix Prevents Loss of ChAT Expression in Basal Forebrain Neurons following a Fimbria-Fornix Lesion" Experimental Neurology 1990 vol. 110: 39-44.
Jaeger et al. "Polymer Encapsulated Dopaminergic Cell Lines as 'Alternative Neural Grafts'" Progress in Brain Research 1990 vol. 82:41-46.
Kawaguchi et al. "The Role of the Transcriptional Regulator Ptf1a in Converting Intestinal to Pancreatic Progenitors" Nature Genetics 2002 vol. 32: 128-134.
Koch et al. "A Novel Member of the Netrin Family, β-Netrin, Shares Homology with the β Chain of Laminin: Identification, Expression, and Functional Characterization" The Journal of Cell Biology 2000 vol. 151(2): 221-234.
Krapp et al. "The bHLH Protein PTF1-p48 is Essential for the Formation of the Exocrine and the Correct Spatial Organization of the Endocrine Pancreas" Genes & Development 1998 vol. 12: 3752-3763.
Lammert et al. "Induction of Pancreas Differentiation by Signals from Blood Vessels" Science 2001 vol. 294: 564-567.
LeCouter et al. "Angiogenesis-Independent Endothelial Protection of Liver: Role of VEGFR-1" Science 2003 vol. 299: 890-893.
Lévesque et al. "Maintenance of Long-Term Secretory Function by Microencapsulated Islets of Langerhans" Endocrinology 1992 vol. 130(2): 644-650.
Lim, F. "Microencapsulated Islets as Bioartificial Endocrine Pancreas" Science 1980 vol. 210: 908-910.
Liu et al. "Novel Role for Netrins in Regulating Epithelial Behavior During Lung Branching Morphogenesis" Current Biology 2004 vol. 14: 897-905.
Livesey, F.J. "Netrins and Netrin Receptors" CMLS, Cell. Mol. Life Sci. 1999 vol. 56: 62-68.
Lum et al. "Xenografts of Rat Islets into Diabetic Mice" Transplantation 1992 vol. 53: 1180-1183.
Matsumoto et al. "Liver Organogenesis Promoted by Endothelial Cells Prior to Vascular Function" Science 2001 vol. 294:559-563.
Nikolova, M. and Asenov, A. "Surface Flavonoid Aglycones in Newly Studied Plant Species" Natural Product Research 2006 vol. 20(1):103-106.
O'Shea et al. "Prolonged Survival of Transplanted Islets of Langerhans Encapsulated in a Biocompatible Membrane" Biochimica et Biophysica Acta 1984 vol. 804: 133-136.
Qin et al. "Characterization of the Receptors for Axon Guidance Factor Netrin-4 and Identification of the Binding Domains" Mol. Cell. Neurosci. 2007 vol. 34: 243-250.
Red-Horse et al. "Endothelium-Microenvironment Interactions in the Developing Embryo and in the Adult" Developmental Cell 2007 vol. 12: 181-194.
Risau, W. "Mechanisms of Angiogenesis" Nature 1997 vol. 386: 671-674.
Schroeder et al. "Differentiation of Mouse Embryonic Stem Cells to Insulin-Producing Cells" Nature Protocols 2006 vol. 1(2): 495-507.

(Continued)

Primary Examiner — Daniel C Gamett
(74) Attorney, Agent, or Firm — Licata & Tyrrell P.C.

(57) ABSTRACT

Methods for altering pancreatic and liver cell function are provided, wherein the compositions and methods are based on use of netrin-4 or on altering the activity of netrin-4.

2 Claims, 10 Drawing Sheets

OTHER PUBLICATIONS

Sefton et al. "Microencapsulation of Mammalian Cells in a Water-Insoluble Polyacrylate by Coextrustion and Interfacial Precipitation" Biotechnology and Bioengineering 1987 vol. 29: 1135-1143.

Shalaby et al. "Failure of Blood-Island Formation and Vasculogenesis in Flk-1-Deficient Mice" Nature 1995 vol. 376: 62-66.

Shim et al. "Directed Differentiation of Human Embryonic Stem Cells Towards a Pancreatic Cell Fate" Diabetologia 2007 vol. 50: 1228-1238.

Sugamori, M.E. and Sefton, M.V. "Microencapsulation of Pancreatic Islets in a Water Insoluble Polyacrylate" Trans Am Soc Artif Intern Organs 1989 vol. 35: 791-799.

Yin et al. "Identification and Expression of Mouse Netrin-4" Mechanisms of Development 2000 vol. 96: 115-119.

Yoshitomi, H. and Zaret, K.S. "Endothelial Cell Interactions Initiate Dorsal Pancreas Development by Selectively Inducing the Transcription Factor Ptf1a" Development 2003 vol. 131(4): 807-817.

Zhang et al. "Identification of a Novel Alternative Splicing Form of Human Netrin-4 and Analyzing the Expression Patterns in Adult Rat Brain" Molecular Brain Research 2004 vol. 130: 68-80.

Cardoso W.V. and Lü, J. "Regulation of Early Lung Morphogenesis: Questions, Facts and Controversies" Development 2006 vol. 133: 1611-1624.

Elghazi et al. "Role for FGFR2IIIb-Mediated Signals in Controlling Pancreatic Endocrine Progenitor Cell Proliferation" PNAS 2002 vol. 99(6): 3884-3889.

Yerba et al. "Recognition of the Neural Chemoattractant Netrin-1 by Integrins $\alpha 6\beta 1$ and $\alpha 3\beta 1$ Regulates Epithelial Cell Adhesion and Migration" Developmental Cell 2003 vol. 5: 695-707.

* cited by examiner

```
  1 MGSCARLLLL WGCTVVAAGL SGVAGVSSRC EKACNPRMGN LALGRKLWAD TTCGQNATEL
 61 YCFYSENTDL TCRQPKCDKC NAAYPHLAHL PSAMADSSFR FPRTWWQSAE DVHREKIQLD
121 LEAEFYFTHL IVMFKSPRPA AMVLDRSQDF GKTWKPYKYF ATNCSATFGL EDDVVKKGAI
181 CTSKYSSPFP CTGGEVIFKA LSPPYDTENP YSAKVQEQLK ITNLRVQLLK RQSCPCQRND
241 LNEEPQHFTH YAIYDFIVKG SCFCNGHADQ CIPVHGFRPV KAPGTFHMVH GKCMCKHNTA
301 GSHCQHCAPL YNDRPWEAAD GKTGAPNECR TCKCNGHADT CHFDVNVWEA SGNRSGGVCD
361 DCQHNTEGQY CQRCKPGFYR DLRRPFSAPD ACKPCSCHPV GSAVLPANSV TFCDPSNGDC
421 PCKPGVAGRR CDRCMVGYWG FGDYGCRPCD CAGSCDPITG DCISSHTDID WYHEVPDFRP
481 VHNKSEPAWE WEDAQGFSAL LHSGKCECKE QTLGNAKAFC GMKYSYVLKI KILSAHDKGT
541 HVEVNVKIKK VLKSTKLKIF RGKRTLYPES WTDRGCTCPI LNPGLEYLVA GHEDIRTGKL
601 IVNMKSFVQH WKPSLGRKVM DILKRECK
```

FIG. 11

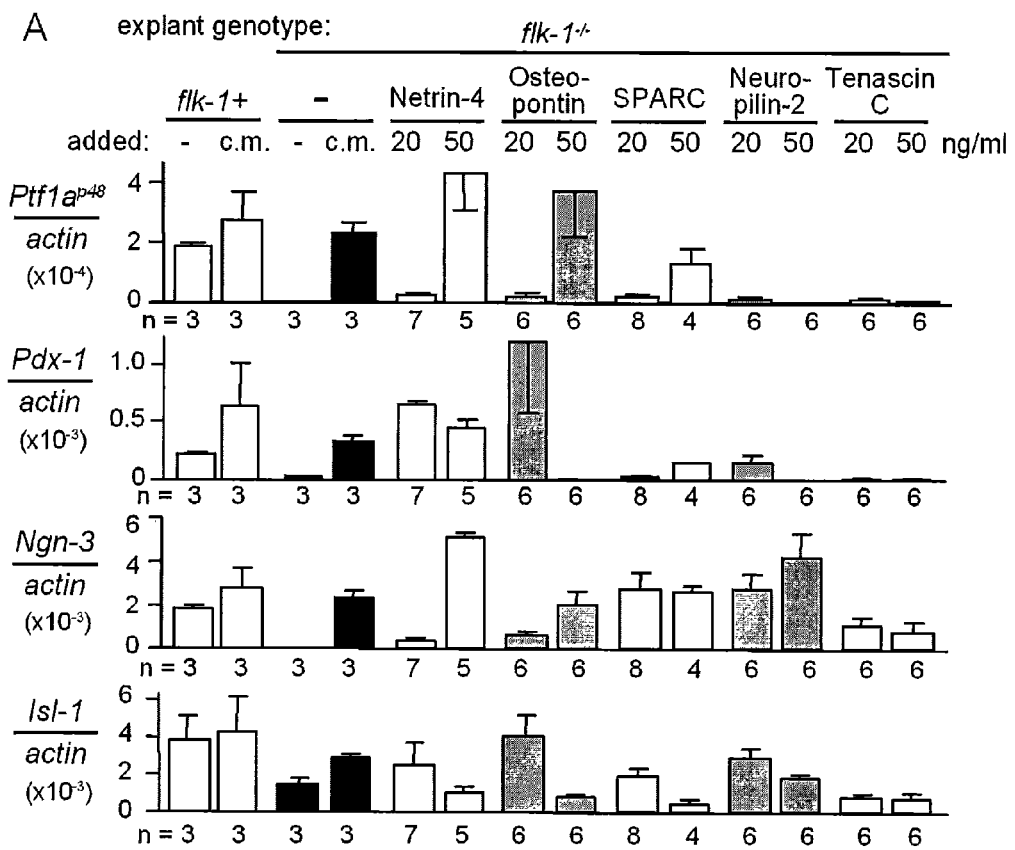

FIG. 12A

SEQUENCE LISTING

```
<160> NUMBER OF SEQ ID NOS: 1

<210> SEQ ID NO 1
<211> LENGTH: 628
<212> TYPE: PRT
<213> ORGANISM: Homo sapiens

<400> SEQUENCE: 1

Met Gly Ser Cys Ala Arg Leu Leu Leu Trp Gly Cys Thr Val Val
1               5                   10                  15

Ala Ala Gly Leu Ser Gly Val Ala Gly Val Ser Ser Arg Cys Glu Lys
                20                  25                  30

Ala Cys Asn Pro Arg Met Gly Asn Leu Ala Leu Gly Arg Lys Leu Trp
                35                  40                  45

Ala Asp Thr Thr Cys Gly Gln Asn Ala Thr Glu Leu Tyr Cys Phe Tyr
            50                  55                  60

Ser Glu Asn Thr Asp Leu Thr Cys Arg Gln Pro Lys Cys Asp Lys Cys
65                  70                  75                  80

Asn Ala Ala Tyr Pro His Leu Ala His Leu Pro Ser Ala Met Ala Asp
                85                  90                  95

Ser Ser Phe Arg Phe Pro Arg Thr Trp Trp Gln Ser Ala Glu Asp Val
                100                 105                 110

His Arg Glu Lys Ile Gln Leu Asp Leu Glu Ala Glu Phe Tyr Phe Thr
            115                 120                 125

His Leu Ile Val Met Phe Lys Ser Pro Arg Pro Ala Ala Met Val Leu
        130                 135                 140

Asp Arg Ser Gln Asp Phe Gly Lys Thr Trp Lys Pro Tyr Lys Tyr Phe
145                 150                 155                 160

Ala Thr Asn Cys Ser Ala Thr Phe Gly Leu Glu Asp Asp Val Val Lys
                165                 170                 175
```

-continued

```
Lys Gly Ala Ile Cys Thr Ser Lys Tyr Ser Ser Pro Phe Pro Cys Thr
            180                 185                 190

Gly Gly Glu Val Ile Phe Lys Ala Leu Ser Pro Pro Tyr Asp Thr Glu
            195                 200                 205

Asn Pro Tyr Ser Ala Lys Val Gln Glu Gln Leu Lys Ile Thr Asn Leu
210                 215                 220

Arg Val Gln Leu Leu Lys Arg Gln Ser Cys Pro Cys Gln Arg Asn Asp
225                 230                 235                 240

Leu Asn Glu Glu Pro Gln His Phe Thr His Tyr Ala Ile Tyr Asp Phe
                245                 250                 255

Ile Val Lys Gly Ser Cys Phe Cys Asn Gly His Ala Asp Gln Cys Ile
            260                 265                 270

Pro Val His Gly Phe Arg Pro Val Lys Ala Pro Gly Thr Phe His Met
            275                 280                 285

Val His Gly Lys Cys Met Cys Lys His Asn Thr Ala Gly Ser His Cys
    290                 295                 300

Gln His Cys Ala Pro Leu Tyr Asn Asp Arg Pro Trp Glu Ala Ala Asp
305                 310                 315                 320

Gly Lys Thr Gly Ala Pro Asn Glu Cys Arg Thr Cys Lys Cys Asn Gly
                325                 330                 335

His Ala Asp Thr Cys His Phe Asp Val Asn Val Trp Glu Ala Ser Gly
            340                 345                 350

Asn Arg Ser Gly Gly Val Cys Asp Asp Cys Gln His Asn Thr Glu Gly
            355                 360                 365

Gln Tyr Cys Gln Arg Cys Lys Pro Gly Phe Tyr Arg Asp Leu Arg Arg
    370                 375                 380

Pro Phe Ser Ala Pro Asp Ala Cys Lys Pro Cys Ser Cys His Pro Val
385                 390                 395                 400

Gly Ser Ala Val Leu Pro Ala Asn Ser Val Thr Phe Cys Asp Pro Ser
                405                 410                 415

Asn Gly Asp Cys Pro Cys Lys Pro Gly Val Ala Gly Arg Arg Cys Asp
            420                 425                 430

Arg Cys Met Val Gly Tyr Trp Gly Phe Gly Asp Tyr Gly Cys Arg Pro
            435                 440                 445

Cys Asp Cys Ala Gly Ser Cys Asp Pro Ile Thr Gly Asp Cys Ile Ser
    450                 455                 460

Ser His Thr Asp Ile Asp Trp Tyr His Glu Val Pro Asp Phe Arg Pro
465                 470                 475                 480

Val His Asn Lys Ser Glu Pro Ala Trp Glu Trp Glu Asp Ala Gln Gly
                485                 490                 495

Phe Ser Ala Leu Leu His Ser Gly Lys Cys Glu Cys Lys Glu Gln Thr
            500                 505                 510

Leu Gly Asn Ala Lys Ala Phe Cys Gly Met Lys Tyr Ser Tyr Val Leu
            515                 520                 525

Lys Ile Lys Ile Leu Ser Ala His Asp Lys Gly Thr His Val Glu Val
    530                 535                 540

Asn Val Lys Ile Lys Lys Val Leu Lys Ser Thr Lys Leu Lys Ile Phe
545                 550                 555                 560

Arg Gly Lys Arg Thr Leu Tyr Pro Glu Ser Trp Thr Asp Arg Gly Cys
                565                 570                 575

Thr Cys Pro Ile Leu Asn Pro Gly Leu Glu Tyr Leu Val Ala Gly His
            580                 585                 590

Glu Asp Ile Arg Thr Gly Lys Leu Ile Val Asn Met Lys Ser Phe Val
    595                 600                 605
```

```
Gln His Trp Lys Pro Ser Leu Gly Arg Lys Val Met Asp Ile Leu Lys
    610                 615                 620

Arg Glu Cys Lys
625
```

COMPOSITIONS AND METHODS FOR ALTERING PANCREAS OR LIVER FUNCTION

This patent application is the National Stage of International Application No. PCT/US2008/060726 filed Apr. 18, 2008, which claims the benefit of priority from U.S. Provisional Ser. No. 60/915,727 filed May 3, 2007, teachings of each of which are herein incorporated by reference in their entirety.

BACKGROUND OF THE INVENTION

Netrins are a family of molecules that were first shown to be involved in axon guidance in brain tissue (Guthrie, S. 1997. *Curr. Biol.* 7:R6-R9; Livesey, F. J. 1999. *Cell. Mol. Life. Sci.* 56:62-68). Netrins act as either attractants or repellants depending on the type of netrin receptors expressed on growth cones (Koch, M. et al. 2000. *J. Cell Biol.* 151:221-234). Several netrins have been identified and named netrin-1, netrin-2, netrin-3 and netrin-4. Only netrin-1, netrin-3 and netrin-4 have been linked to human physiology and development. Netrins 1 through 3 are structurally-related to the short arms of laminin-gamma chains, while netrin-4, also known as beta-netrin, has been shown to related to the laminin-beta chains (Koch, M. et al. 2000. *J. Cell Biol.* 151:221-234).

Studies have shown that netrin-4 is expressed in various areas of the nervous system and that this protein plays a role in neurite outgrowth. Recent studies have shown that netrin-4 is widely expressed in human and mouse tissues, having been detected in spleen, prostate, ovary, heart, kidney, pancreas, mammary gland, and uterus (Koch, M. et al. 2000. *J. Cell Biol.* 151:221-234). Other physiological roles have been discussed in association with netrin-4 including promotion of neuronal plasticity in adult brain (Zhang, C. et al. 2004. *Brain Res. Mol. Brain. Res.* 130:68-80), lung development (Liu, Y. et al. 2004. *Curr. Biol.* 14:897-905), and axon growth and migration (Qin, S. et al. 2007. *Mol. Cell. Neurosci.* 34:243-250).

Additionally, U.S. Patent Application 2003/0207347 describes a role for netrin-4 proteins or polypeptides in the development and/or regeneration of the nervous system. Netrin-4 activities disclosed include the ability to modulate neurite outgrowth, guidance, and/or stability; the ability to modulate development of the central nervous system, including development of the spinal cord, development of the optic system, and development of the olfactory system; the ability to modulate development of areas of the brain; the ability to modulate angiogenesis, including inhibition of angiogenesis in tumors; the ability to modulate proliferative disorders such as cancer; the ability to modulate development of the kidney, including morphogenesis of tubules and glomeruli; the ability to modulate the maturation of ovarian follicles; and the ability to modulate muscular development and/or innervation, especially smooth muscle. A related application, U.S. Patent Application 2004/0248178, further describes specific roles for netrin-4 and variants of netrin-4 in modulating kidney, ovary, heart, or muscle development.

Another U.S. Patent Application (2006/0019896) discloses uses of netrin-4 for the promotion of angiogenesis, promotion of migration of endothelial cells and smooth muscle cells, promotion of stem cell proliferation, decreasing inflammation, inhibiting tumor growth, preventing and treating adhesions, and treatment of neuropathy. U.S. Patent Application 2006/0025335 discloses use of netrin-4 to modulate inflammatory cell movement and then the treatment of patients with adverse immune responses. The application links netrin-4-related alterations in inflammatory cell movement to treatment of dozens of immune system diseases. Finally, WO/2006/054000 describes mutated netrin-4 molecules and their use as therapeutics to prevent and treat cancer.

The specific cellular events linked to netrin-4 and its potential effects in humans are under investigation. It has now been found that netrin-4 acts as a signaling molecule secreted from endothelial cells and is capable of inducing pancreatic and liver cell differentiation in embryonic cells, thereby having the ability to alter pancreatic and liver cell function.

SUMMARY OF THE INVENTION

An object of the present invention is a method for inducing differentiation of an endodermal cell or a progenitor cell into a pancreatic or liver cell which comprises contacting an endodermal cell or a progenitor cell with an effective amount of netrin-4 thereby inducing differentiation of the endodermal cell or the progenitor cell into a pancreatic or liver cell. Also contemplated by the present invention is a method wherein the cell is a partially differentiated liver or pancreatic progenitor cell.

Another object of the present invention is a method for altering pancreatic or liver cell function which comprises contacting a pancreatic or liver cell with an effective amount of netrin-4, wherein contact of the cell with netrin-4 results in an alteration in the function of the pancreatic or liver cell.

Another object of the present invention is a method for altering pancreatic or liver cell function which comprises contacting a pancreatic or liver cell with an effective amount of a composition comprising a netrin-4 protein, a netrin-4 antibody, a netrin-4 mimetic, a netrin-agonist, a netrin-4 antagonist, a mutated netrin-4 protein, or a netrin-4 variant or fragment thereof, formulated in a pharmaceutically acceptable vehicle, wherein contact of the cell with said composition results in an alteration in the function of the pancreatic or liver cell.

Another object of the present invention is a method for preventing or treating a disease of the pancreas or liver in a patient comprising administering to a patient a therapeutically effective amount of a composition comprising netrin-4 formulated in a pharmaceutically acceptable vehicle, wherein administration of said composition results in prevention or treatment of a disease of the pancreas or liver. In a preferred embodiment the disease is diabetes mellitus.

Another object of the present invention is a method for preventing or treating a disease of the pancreas or liver in a patient which comprises administering to a patient a therapeutically effective amount of a composition comprising a netrin-4 protein, netrin-4 antibody, a netrin-mimetic, a netrin-4 agonist, a netrin-4 antagonist, a mutated netrin-4 protein, or a netrin-4 variant or fragment thereof, formulated in a pharmaceutically acceptable vehicle, wherein administration of the composition results in prevention or treatment of a disease of the pancreas or liver.

Yet another object of the present invention is a method of restoring function of a damaged pancreatic or liver tissue which comprises contacting a damaged pancreas or liver tissue with an effective amount of netrin-4, wherein contact of the damaged tissue with netrin-4 results in a restoration of function of the damaged tissue.

Finally, other objects of the present invention include isolated pancreatic or liver cells differentiated by the method of the present invention as well as pharmaceutical compositions which comprise isolated pancreatic or liver cells differentiated by the method of the present invention and a pharmaceutically acceptable vehicle.

DESCRIPTION OF THE DRAWINGS

FIGS. 1A through 1D depict PECAM-CD31 immunohistochemistry. A CD-31 vascular network is reconstructed by the co-culture of eEND2 cells with the flk-1$^{-/-}$ explants.

FIG. 2 depicts the results of experiments with RT-PCR cycle step analysis.

FIG. 5 depicts the results of experiments using eEND2 conditioned medium. Using a 10K cutoff filter in an ultracentrifugation process to separate components of the conditioned medium, ptf1a$^{p48}$ and pdx activity was discovered in the 10K retenate and not the 10K flow-through.

FIG. 11 depicts the amino acid sequence for netrin-4 (SEQ ID NO:1).

FIG. 12 depicts results showing that netrin-4 is sufficient to induce dorsal pancreatic endoderm differentiation. FIG. 12A depicts results from a qRT-PCR assay of gene expression that normalized signals to actin mRNA. It shows that purified proteins, at the amounts indicated, induced the expression of several known explant tissue differentiation genes (ptf1a$^{p48}$, pdk-1, Isl-1, ngn-3).

FIG. 14 depicts the effects of treatment with netrin-4 on induction of albumin and alpha-fetoprotein expression in liver bud explants from flk-1$^{-/-}$ embryos. FIG. 14A depicts the effects of netrin-4 on albumin while

DETAILED DESCRIPTION OF THE INVENTION

Figure 1:
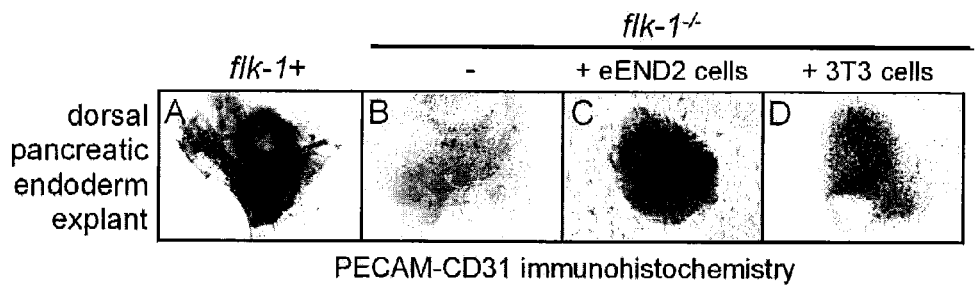
FIG. 1 depicts the growth of tissue explants of dorsal pancreatic endoderm, both wild-type flk-1+ and flk-1$^{-/-}$, when co-cultured with various types of cells.

It has become evident that signaling from endothelial cells can promote the differentiation, growth and homeostasis of diverse tissues outside the cardiovascular system, independent of endothelial cell function as a conduit for substances in the bloodstream. Despite the diversity of endothelial cell signaling in gut organ development, the identity of relevant signaling molecules has been unclear. Using a combination of genetics, embryology, biochemical purification and proteonomics, individual signaling molecules have been identified that are secreted from endothelial cell lines and induce aspects of pancreatic and liver cell differentiation of endoderm cells. One such molecule that has been identified is netrin-4. Therefore, the present invention includes methods for modulation of pancreatic cell and liver cell differentiation that involve modulating activity of netrin-4.

Specific applications of the present invention include use of netrin-4, or compounds that modulate netrin-4 activity, to affect pancreatic and liver cell differentiation and ultimately pancreatic or liver cell function. In the context of the present invention, compounds that lead to "modulation of netrin-4 activity" include compounds that lead to either an increase or a decrease in the activity of netrin-4 in pancreatic or liver cells. Such compounds contemplated by the present invention include compounds that act as netrin-4 agonists or antagonists, antibodies to netrin-4, netrin-4 mimetics, mutated netrin-4 proteins, or netrin-4 variants or fragments. Use of compounds that modulate netrin-4 activity, or use of netrin-4 itself, in methods of the present invention will lead to alterations in the function of pancreatic or liver cell function based on the finding that netrin-4 has the ability to alter pancreatic and liver cell differentiation activity.

Reciprocal signaling between endothelial cells and smooth muscle cells, and between endothelial cells and cardiac muscle cells, is necessary for proper development of the cardiovascular system (Risau, 1997. *Nature* 386:671-674). Such signaling involves distinct classes of ligand-receptor interactions, which in some cases also promote neuronal development (Carmeliet and Tessier-Lavigne 2005. *Nature* 436:193-200). Only recently, however, has it been appreciated that endothelial cells signal directly to epithelial cells in gut organs, such as during liver, pancreas and thyroid development as well as during regenerative responses to tissue damage (Cleaver and Melton 2003. *Nat. Med.* 9:661-668; Red-Horse et al. 2007. *Dev. Cell* 12:181-194). Direct signaling refers to signaling from endothelial cells to other cell types, and is not due to endothelial cell function as a conduit for components in the bloodstream. For example, flk-1$^{-/-}$ mouse embryos, which are genetically deficient in endothelial cells (Shalaby et al. 1995. Nature 376:62-66), exhibit major defects in pancreatic endoderm differentiation and liver bud growth (Matsumoto et al. 2001. Science 294:559-563; Lammert et al. 2001. Science 294:564-567; Yoshitomi and Zaret 2004. Development 131:807-817). Co-culture of wild-type aortae with pancreatic endoderm tissue from flk-1$^{-/-}$, in the absence of blood flow, is sufficient to restore differentiation (Yoshitomi and Zaret 2004. Development 131:807-817). Similarly, liver bud growth in vitro is markedly enhanced by resident endothelial cells (Matsumoto et al. 2001. Science 294:559-563. Hepatocyte growth factor (HGF) produced from endothelial cells can promote regeneration after liver cell damage (LeCouter et al. 2003. Science 299:890-893) and extracellular matrix proteins produced from endothelial cells can help maintain adult pancreatic islet function (Nikolova et al. 2006. Nat. Prod. Res. 20:103-106). Given the emerging contexts of direct endothelial cell signaling in gut organ biology and organogenesis, and the potential for applying the knowledge to directed cell differentiation and regenerative medicine, the identity of endothelial proteins that promote early pancreas and liver organogenesis was sought.

Experiments were performed to isolate and identify putative endothelial cell signaling molecules. Four endothelial cell lines were used in the experiments (eEND2, bEND-3, HUVEC and HUAEC) as well as two control cell lines (3T3 and 293T). The cell lines were screened for the existence of compounds that had the ability to restore parameters of gut organ development in flk-1$^{-/-}$ tissue explant assays.

Dorsal pancreatic endoderm and liver buds were microdissected from mouse embryos of flk-1$^{+/-}$ and flk-1$^{-/-}$ genotypes at nine days gestation (E9.0) and cultured on a Transwell membrane at the air-liquid interface as previously described (Matsumoto et al. 2001. Science 294:559-563; Yoshitomi and Zaret 2004. Development 131:807-817), in the presence and absence of cell lines previously seeded onto the membrane. Results showed that eEND2 cells, a permanent mouse endothelial cell line, were able to integrate into the flk-1$^{-/-}$ tissues and generate a CD-31 positive network of cells that resembled the native vascular network generated in wild-type tissue explants (FIG. 1A). Similar results were obtained with co-culture of bEND-3 cells and HUAEC endothelial cell lines. In contrast, 3T3 control cells, a non-endothelial cell line, were not able to integrate into the flk-1$^{-/-}$ tissues, nor did the control cells result in generation of a vascular network that resembled wild-type tissue explants (FIG. 1). HUVEC cell co-culture with flk-1$^{-/-}$ tissues produced results similar to the 3T3 control cells. The presence of endothelial cells did not markedly affect the overall growth of the epithelial cells in the tissue explant (FIGS. 1B and 1C). These data demonstrated that co-culture of endothelial cells with the endothelial-cell deficient flk-1$^{-/-}$ tissue affected the development of the tissues, implicating substances present in or produced by the endothelial cells in the altered cellular physiology.

Figure 2A:
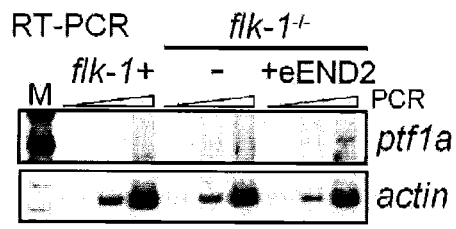
FIGS. 2A and 2B respectively show results where eEND2 or 3T3 cells are co-cultured with flk-1$^{-/-}$ dorsal pancreatic endoderm explants. Only in the co-culture with eEND2 is the expression of the ptf1a$^{p48}$ gene detected.
Figure 2B:
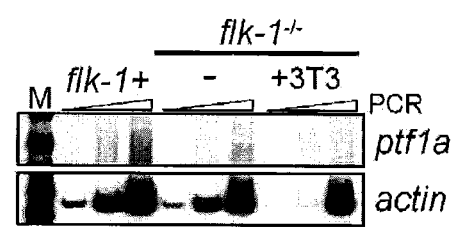

Experiments were then performed to identify gene expression changes in the co-cultured cells as a first step in identifying the putative endothelial cell signaling molecules. RT-PCR cycle step analysis showed that co-culture of eEND2 cells with flk-1$^{-/-}$ dorsal pancreatic endoderm explants dramatically enhanced expression of the ptf1a$^{p48}$ gene (FIG. 2A), whereas co-culture of the explants with 3T3 cells failed to enhance expression of this gene (FIG. 2B). Expression of ptf1a$^{p48}$ was not detected in flk+ explants (FIG. 2) The ptf1a$^{p48}$ gene encodes a transcription factor that is induced in wild-type embryos at very low levels at E9.0 (Yoshitomi and Zaret 2004. Development 131:807-817), yet is crucial for subsequent pancreatic differentiation (Krapp et al. 1998. Genes Dev. 12:3752-3763; Kawaguichi et al. 2002. Nat. Genet. 32:128-134). Further, it has been shown that ptf1a$^{p48}$ expression in the dorsal pancreatic endoderm, but not the expression of various other pancreatic regulatory factors, is critically dependent upon cell interactions with the aortic endothelium (Yoshitomi and Zaret 2004. Development 131:807-817). Considered together, these results demonstrated that endothelial cell lines were able to complement the genetic deficiency of endogenous vascular cells in flk-1$^{-/-}$ tissue explants and promote an early step of pancreatic differentiation.

Figure 3:
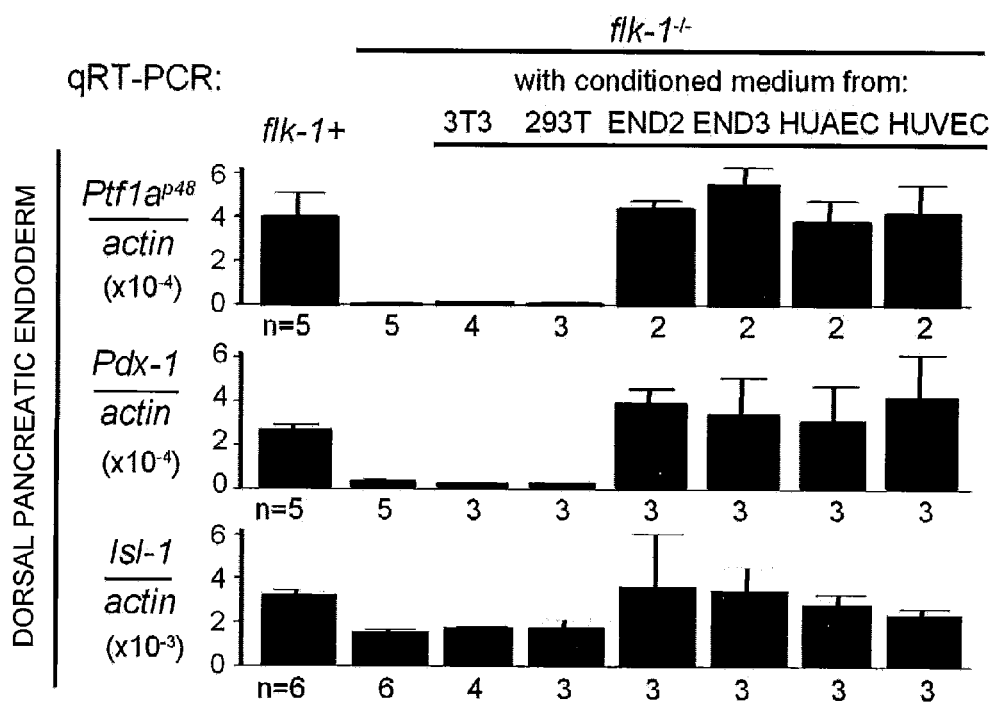
FIG. 3 depicts results from a more sensitive qRT-PCR assay of gene expression that normalized signals to actin mRNA. Conditioned medium from various endothelial cell lines, but not the control cell lines, induced the expression of several known explant tissue differentiation genes (ptf1a$^{p48}$, pdk-1, Isl-1).
Figure 4:
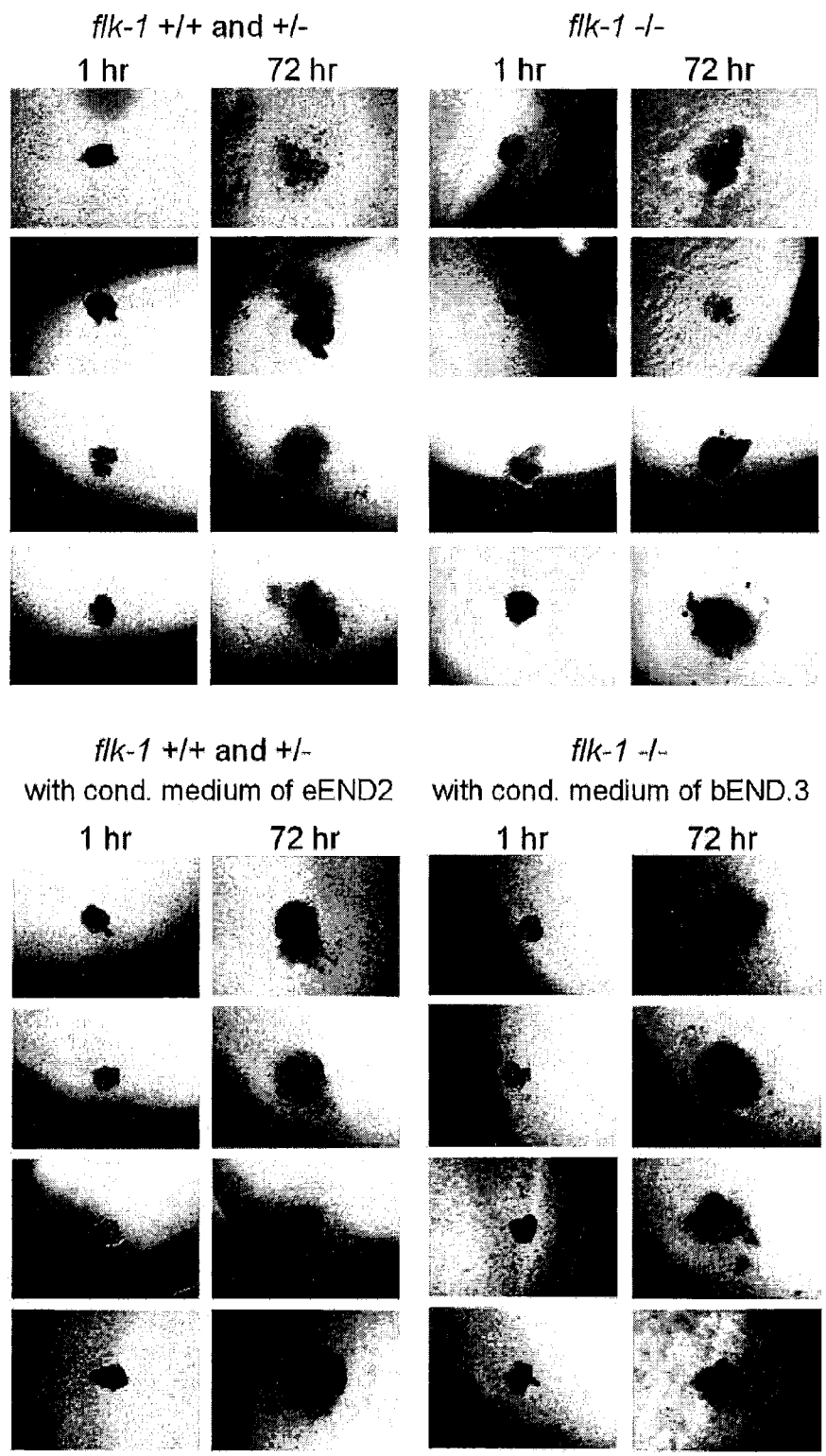
FIG. 4 depicts the growth of dorsal pancreatic endoderm explants in the presence of conditioned medium from the endothelial cell lines.

To define the nature of the interactions between endothelial cells and tissue explants as involving putative signaling molecules as opposed to some other type of cell-cell interaction, studies were performed with medium collected from endothelial cell lines. A more sensitive qRT-PCR assay of gene expression was developed that normalized signals to actin mRNA. Conditioned medium was obtained by culturing the cell lines in plastic dishes to near confluence, washing the cells extensively, cultivating the cells with basal (DMEM) medium without serum or added growth factors for two days, and collecting and filtering the medium. Results showed that conditioned medium from the endothelial cell lines, but not the control cell lines, was sufficient to induce the expression of several known explant tissue differentiation genes (FIG. 3). The expression of such genes was markedly enhanced (near levels of wild-type explants, flk-1$^+$) only when conditioned medium of endothelial cell lines was used. Moreover, the conditioned medium from the endothelial cell lines had this effect without affecting overt explant growth and replication rate (FIG. 4). A 1:1 mix (approximately 50 micrograms) of conditioned medium from all four endothelial cell lines, but none of the control cell lines, combined with normal culture medium (Yoshitomi and Zaret 2004. Development 131:807-817) restored expression of ptf1a$^{p48}$ in flk-1$^{-/-}$ dorsal pancreatic endoderm explants (FIG. 3, top panel) Expression of ptf1a$^{p48}$ is normally induced in cells that are positive for the PDX-1 homeobox transcription factor (Kawaguichi et al. 2002; Chiang and Melton 2003. Dev. Cell 4:383-393; Yoshitomi and Zaret 2004. Development 131:807-817). Results also showed that the endothelial conditioned medium also restored pdx-1 expression to normal levels (FIG. 3, middle panel). Expression of Isl-1, which is primarily observed in the pancreatic mesenchyme at the E9.0 stage (Ahlgren et al. 1997. Nature 385:257-260) was not markedly affected by the presence or the endothelial conditioned medium (FIG. 3, bottom panel). Therefore, proteins released or secreted from endothelial cell line cultures (putative endothelial signaling molecules) were sufficient to complement a deficiency in endothelial inductive activity in flk-1$^{-/-}$ tissue explants.

Figure 5:
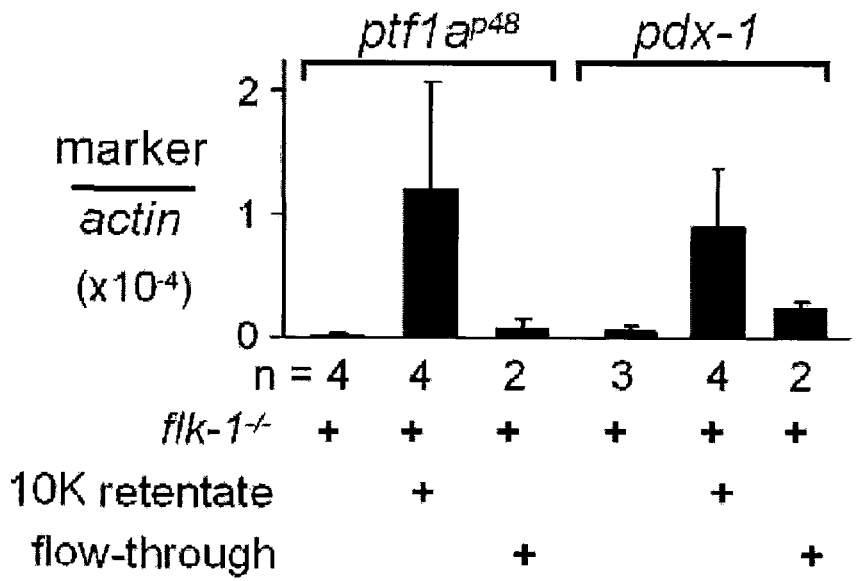
Figure 6:
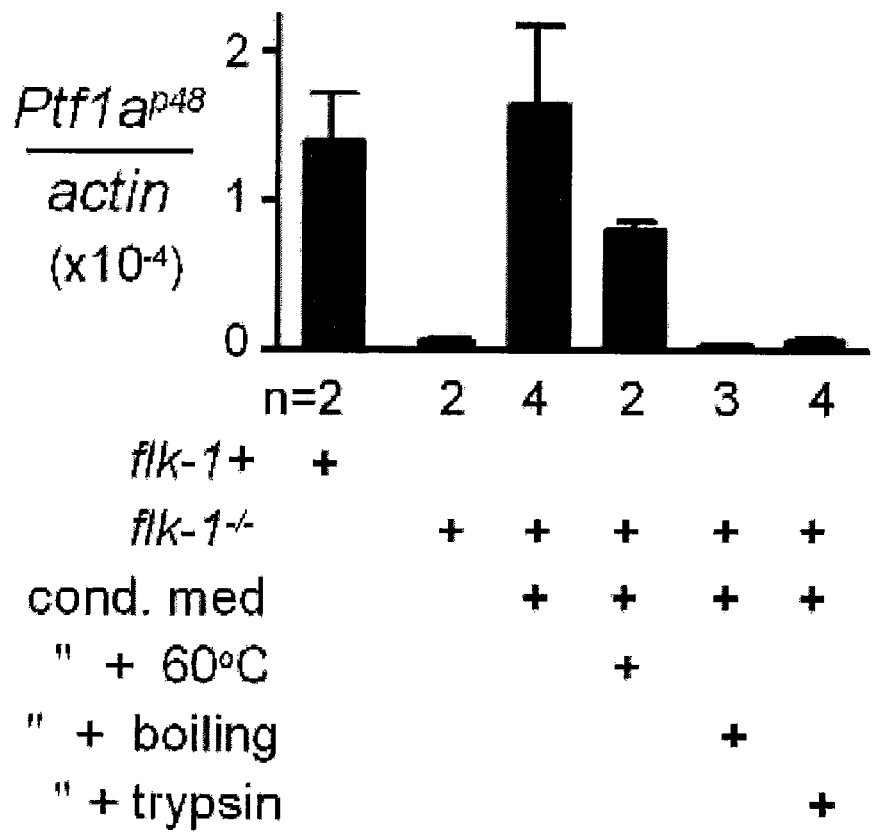
FIG. 6 depicts results of experiments using eEND2 conditioned medium where ptf1a$^{p48}$ activity was measured after incubating retenate for 10 minutes at 60° C. or by boiling or trypsin treatment. Induction of ptf1a$^{p48}$ was inhibited by boiling or trypsin treatment, consistent with the induction being mediated by a protein.
Figure 7:
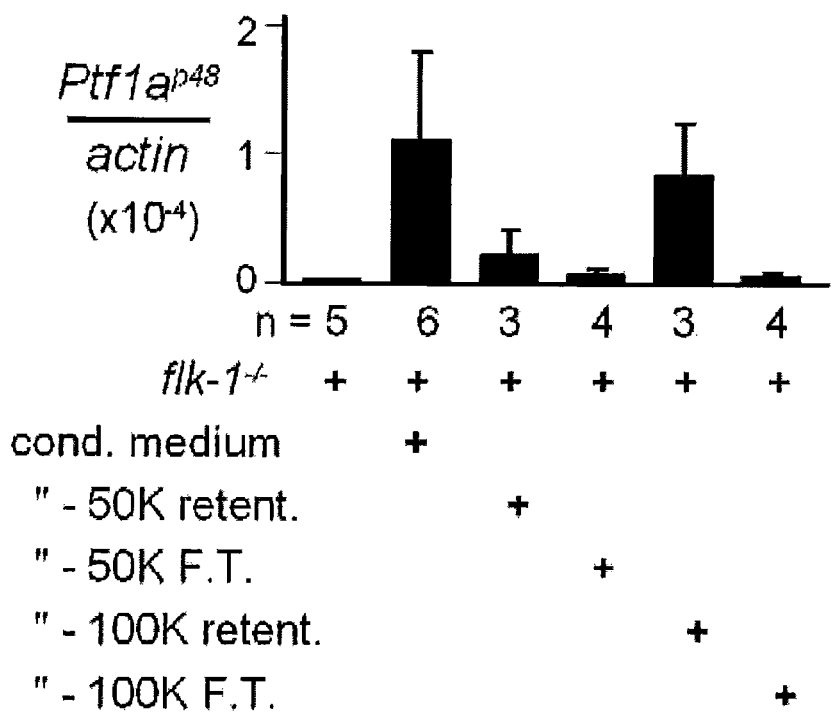
FIG. 7 depicts results of experiments using eEND2 conditioned medium where ptf1a$^{p48}$ activity was measured after passage through either 50K or 100K filters. The ptf1a$^{p48}$ induction activity was successively retained on the filters in 50K and 100K ultracentrifugation assays, indicating that it depends upon a large molecule or complex.

With these results, experiments were undertaken to further characterize the endothelial signaling molecules that were present in the conditioned medium. The experiments were performed using eEND2 conditioned medium. Using a 10K cutoff filter in an ultra-centrifugation process to separate components of the conditioned medium, it was shown that ptf1a$^{p48}$ and pdx induction activity was absent in the flow-through but concentrated 25-fold in the retenate (FIG. 5). These data indicated that the active molecules were not free, small molecules. Additional experiments showed that the ptf1a$^{p48}$ induction activity was partially impaired by incubating the retenate for 10 minutes at 60° C. and completely impaired by boiling or trypsin treatment (FIG. 6).

Figure 8:
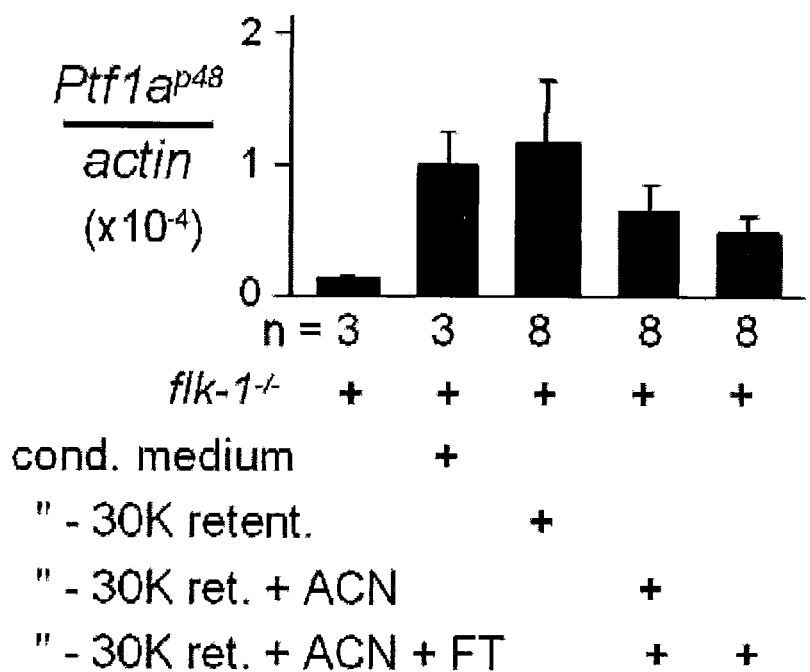
FIG. 8 depicts the results of experiments using eEND2 conditioned medium where ultra-filtration was performed in the presence of 25% acetonitrile and 0.1 M glycine (pH 2.3) to denature proteins, and the retenate was then re-natured, followed by measurement of ptf1a$^{p48}$ activity. The retenate retained 60% of ptf1a$^{p48}$ induction activity and was not enhanced by combination with renatured flow-through material, indicating that the ptf1a$^{p48}$ induction activity is not due to a small molecule bound to a large molecule.
Figure 9:
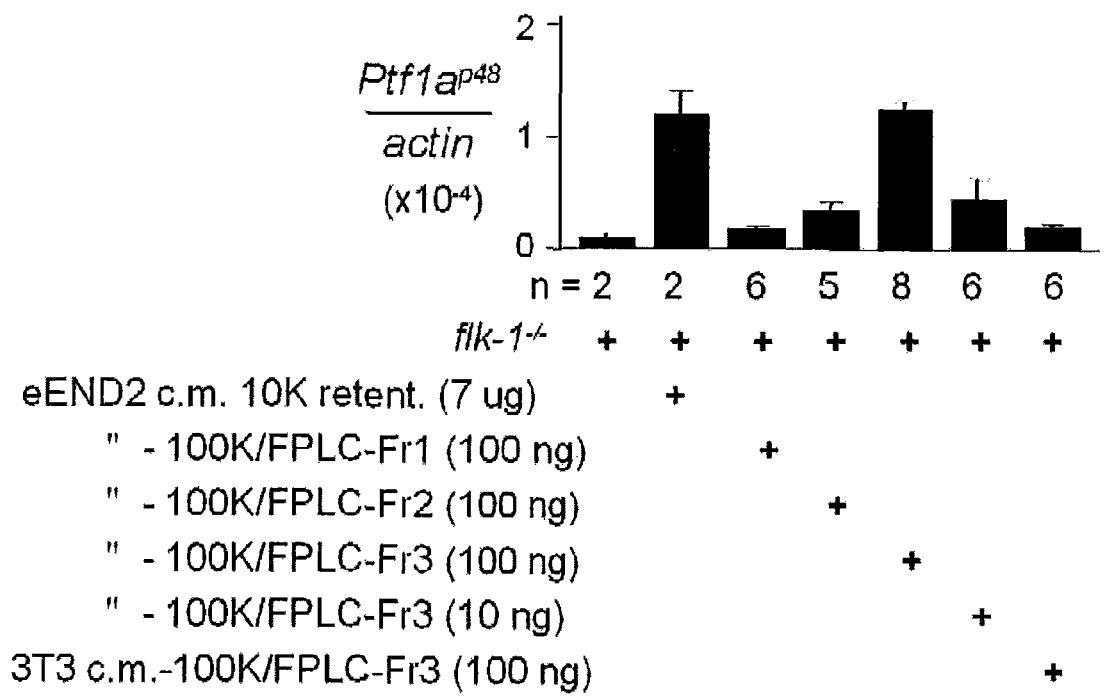
FIG. 9 depicts results or experiments using eEND2 conditioned medium where a 10K retenate was sequentially fractionated at 50K and 100K, and the 100K retenate was fractionated by anion-exchange fast protein liquid chromatography (FPLC), followed by measurement of ptf1a$^{p48}$ activity in collected fractions. The ptf1a$^{p48}$ inducing activity was in the 100K/FPLC-Fr3 fraction.

Ultra-filtration was then performed in the presence of 25% acetonitrile and 0.1 M glycine (pH 2.3) to denature proteins, and the retenate was then re-natured; the retenate retained 60% of ptf1a$^{p48}$ induction activity and was not enhanced by combination with re-natured flow-through material (FIG. 8). These results indicated that the ptf1a$^{p48}$ induction activity was not due to a small molecule bound to a large molecule. Further experiments showed that when a 10K retenate was sequentially fractionated at 50K and 100K, and the 100K retenate was fractionated by anion-exchange fast protein liquid chromatography (FPLC), ptf1a$^{p48}$ induction activity was reproducibly recovered in Fraction-3 (FIG. 9; Fr3), which represented 5% of the input FPLC material. A comparable fraction of 3T3 cell conditioned medium lacked activity (FIG. 9). Based on the fact that 100 ng of the eEND2 100K/FPLC-Fr3 was able to completely restore ptf1a$^{p48}$ expression in flk-1$^{-/-}$ dorsal pancreatic endoderm explants, but a 10 ng sample exhibited only partial activity (FIG. 9), it can be concluded that the activity was enriched over 500-fold from the conditioned medium.

Given the lower complexity of the eEND2, 100K/FPLC-Fr3, four analyses of each were performed with tryptic digests of the 100K/FPLC-Fr3 fractions of eEND2 and 3T3 cells by automated microcapillary liquid chromatography-tandem mass spectrometry (LC-MS/MS), and one analysis one analysis of each was performed by multidimensional protein identification technology (MudPIT) with LC-MS/MS. Two analyses each of tryptic digests of the eEND2, 100K/FPLC-Fr1 and -Fr2 fractions were performed by MudPIT/LC-MS/MS. In addition, spots were excised from the eEND2 100K/FPLC-Fr3 lane and LC-MS/MS was performed. Protein identifications from the diverse approaches were compared and a list of candidate signaling proteins enriched in the active fraction was compiled (Table 1).

Figure 10:
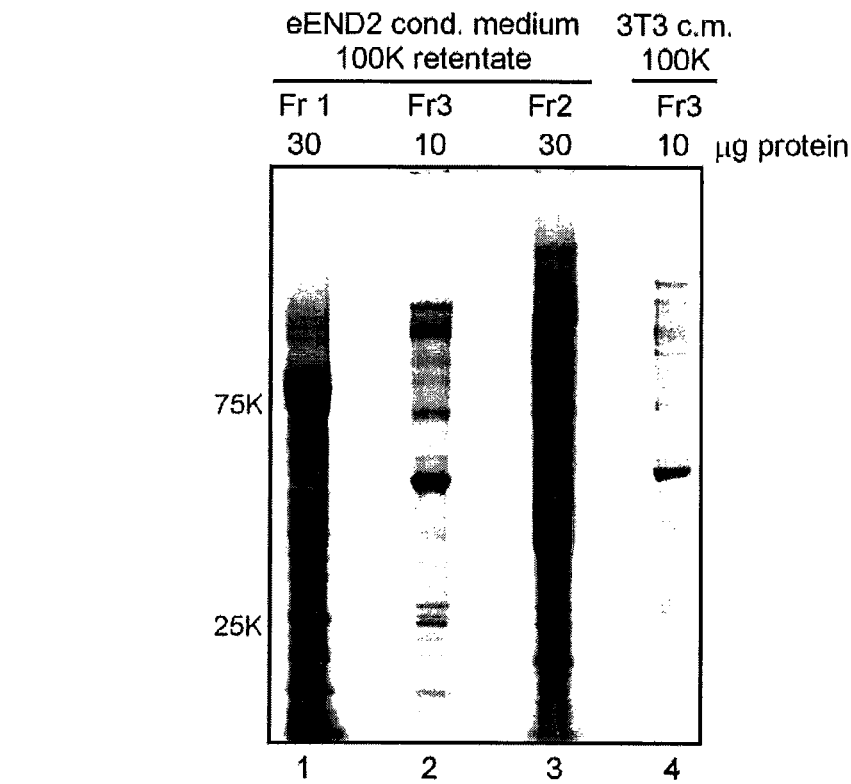
FIG. 10 depicts results of a SDS-PAGE analysis of the active and inactive FPLC fractions from the eEND2 100K retenate and the inactive Fr3 from the 3T3 100K retenate.
Figures 12B, 12C:
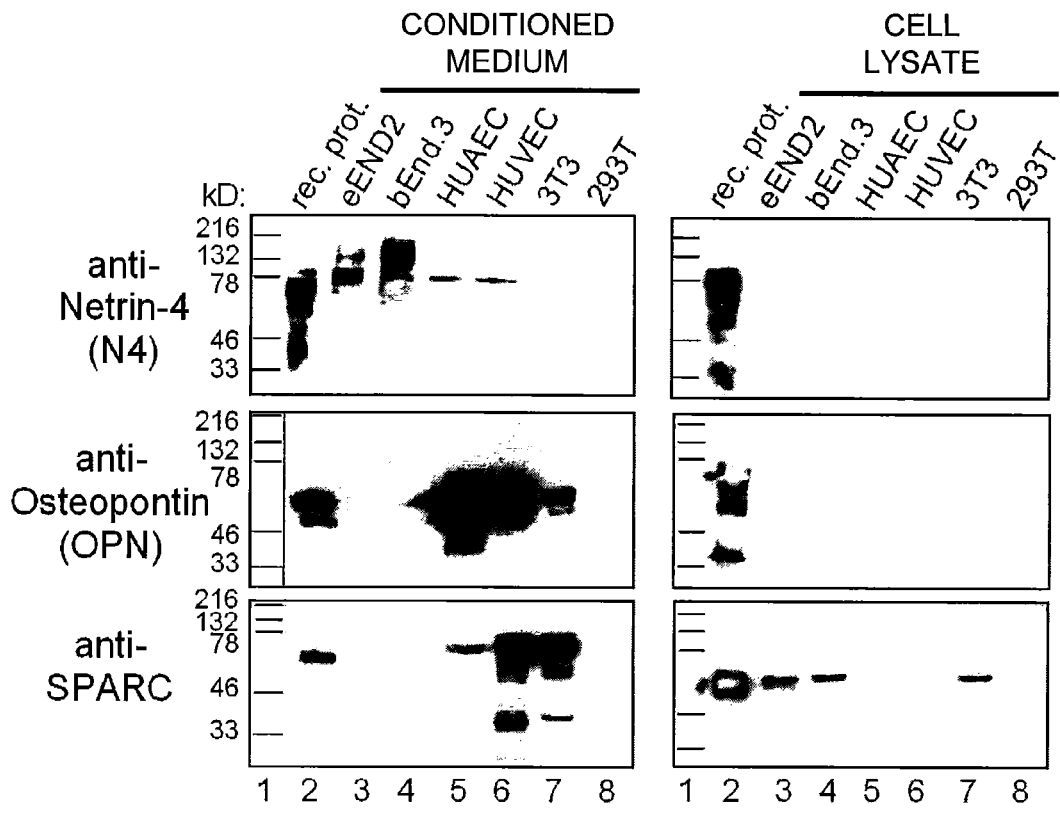
FIG. 12B is a western blot showing that netrin-4 was detected in all of the endothelial cell lines which had ptf1a$^{p48}$ inducing activity and not in the 3T3 and 293T control cell lines which lacked ptf1a$^{p48}$ inducing activity.
FIG. 12C depicts results of a Western blot analysis of proteins in cell lysates.

Experiments were then undertaken to isolate and identify the active protein(s) in the retenate. SDS-PAGE analysis of the active and inactive FPLC fractions from the eEND2 100K retenate and the inactive Fr3 from the 3T3 100K retenate revealed a simple banding pattern in the active eEND2 100K/Fr3 fraction (FIG. 10). The three fractions were then subjected to mass spectroscopic analysis, combined with proteomic studies and protein comparisons The ability of purified, recombinant candidate proteins to substitute for the activity of the eEND2 conditioned medium was tested using each protein in the 20-50 ng/ml range. A 50 ng exposure level of netrin-4 was sufficient to restore ptf1a$^{p48}$ expression in the f/k-1$^{-/-}$ tissue explants of dorsal pancreatic endoderm. Netrin-4 showed variable induction activity with Pdx-1 and Ngn-3 (FIG. 12A). Low concentrations of netrin-4 slightly enhanced Isl-1 expression (FIG. 12A). Western blotting revealed that netrin-4 was detected in the conditioned medium from HUAEC, HUVEC, and 3T3 control cells, but not in that from eEND2 or bEND.3 cells (FIG. 12B).

Figure 12D:
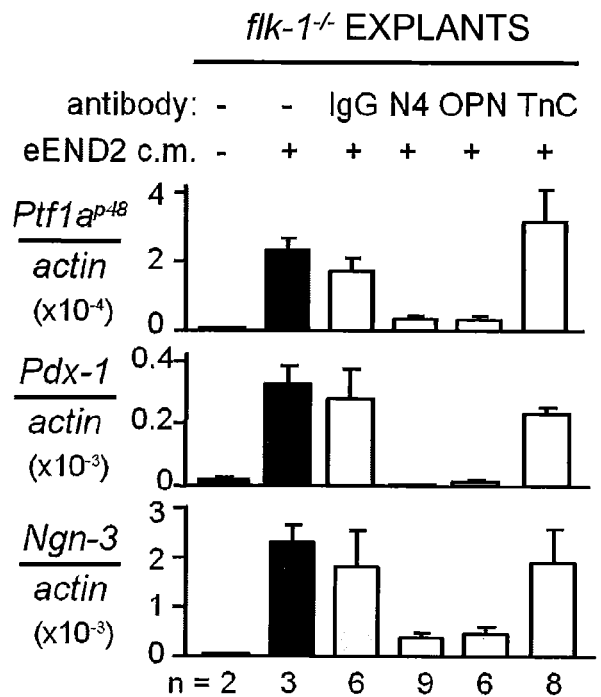
FIG. 12D depicts results showing that antibodies to netrin-4 inhibit the ptf1a$^{p48}$ inducing activity of netrin-4 in conditioned medium.

The antibodies used for Western blotting were then separately added to eEND2 conditioned medium, in order to determine if their respective antigens were necessary for early pancreatic gene induction in the endoderm explant assay. Notably, anti-netrin-4 added to the conditioned medium and cultures inhibited the induction of ptf1a$^{p48}$, pdx-1, and ngn-3 mRNAs in the explants, whereas comparable amounts of control IgG or antibody to Tenascin C had no effect (FIG. 12D). These data indicate that netrin-4 is necessary for the ptf1a$^{p48}$ inducing activity in the conditioned medium.

Figure 13:
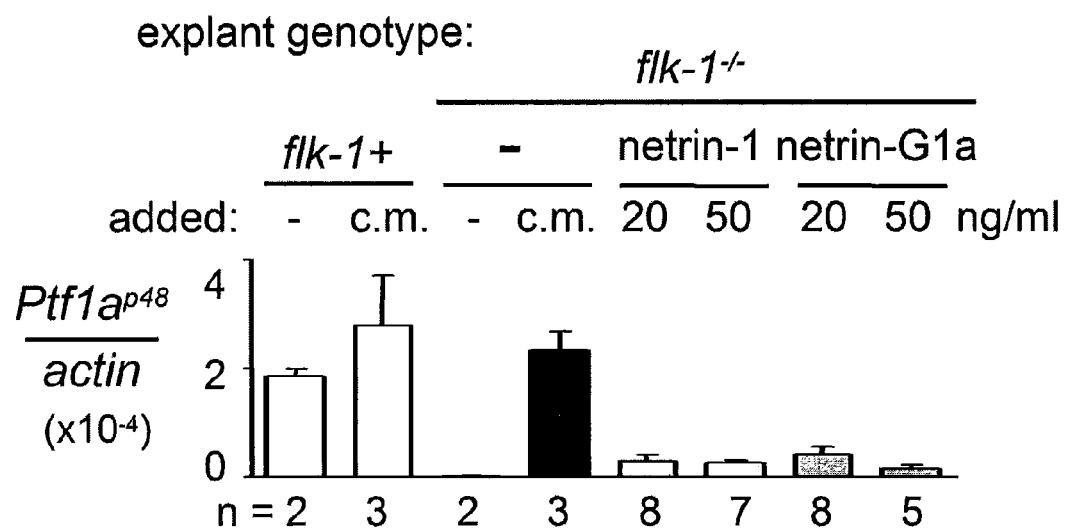
FIG. 13 depicts results of experiments showing that netrin 1 and netrin Gla lack ptf1a$^{p48}$ inducing activity.

Netrins were originally characterized as laminin-related molecules that promote neurite outgrowth and axon pathfinding, but recently have been found to promote the development of the inner ear, mammary gland, lung, and vascular system. Mammals contain three netrin genes, netrin 1, netrin 3, and netrin 4, and the related genes netrin g1 and netrin g2. The data described herein showed that solely netrin-4 (FIG. 12A), and not netrin-1 or Netrin Gla (FIG. 13), stimulated ptf1a$^{p48}$ expression in flk-1$^{-/-}$ dorsal pancreatic endoderm explants. It

TABLE 1

Number of Unique Peptides Identified, Each Experiment

| | LC-MS/MS and MudPIT | | | | | | | | | | | | 1D |
|---|---|---|---|---|---|---|---|---|---|---|---|---|---|
| | Exp't: | | | | | | | | | | | | |
| | Dec. 18, 2006 | | Dec. 23, 2006 | | Jan. 03, 2007 | | | | Jan. 11, 2007 | | | | gel bands |
| | Cell Source: | | | | | | | | | | | | |
| FPLC Fraction | eEND2 | 3T3 | eEND2 | 3T3 | eEND2 | | 3T3 | | eEND2 | | 3T3 | | eEND2 |
| | 2 3 | 3 | 2 3 | 3 | 1 2 | 3 | 3 | | 1 2 | 3 | 3 | | 3 |
| Protein/I.D.: | | | | | | | | | | | | | |
| Netrin-4 IPI00119840.1 | 0 0 | 0 | 0 0 | 0 | 0 0 | 1 | 0 | | 0 0 | 3 | 0 | | 0 |
| Osteopontin IPI00309133.6 | 1 1 | 1 | 1 1 | 1 | 0 0 | 1 | 0 | | 0 0 | 1 | 0 | | 0 |
| SPARC IPI00126343.1 | 0 9 | 0 | 0 11 | 0 | 0 11 | 6 | 0 | | 0 11 | 7 | 0 | | 3 |
| Neuropilin-2 IPO00129911.1 | 0 1 | 0 | 0 2 | 0 | 0 1 | 0 | 0 | | 0 0 | 1 | 0 | | 14 |
| Tenascin C IPI00403938.1 | 0 28 | 0 | 0 36 | 0 | 0 10 | 15 | 0 | | 0 10 | 24 | 0 | | 114 |
| Neogenin IPI00129159.1 | 0 0 | 0 | 0 0 | 0 | 0 7 | 1 | 0 | | 0 7 | 2 | 0 | | 21 | is known that mice lacking netrin-4 are viable (Liu, Y. et al. 2004. *Curr. Biol.* 14:897-905). To determine if these proteins are produced at the E0.9, 15-20 somite pair (S) stage, the period during which ptf1a$^{p48}$ is normally induced, whole mount immunofluorescence was performed on mouse embryos and the positions of the signals relative to the pattern for Pdx-1, which marks the dorsal pancreatic endoderm, were compared. Results showed that netrin-4 was expressed in the heart and visceral tissues, as well as in a trace around the domain of the dorsal pancreatic endoderm. These data indicated that the time and place of expression of netrin-4 is consistent with a role for this molecule in the normal induction of the endogenous ptf1a$^{p48}$ gene during pancreatic development.

Figure 14A:
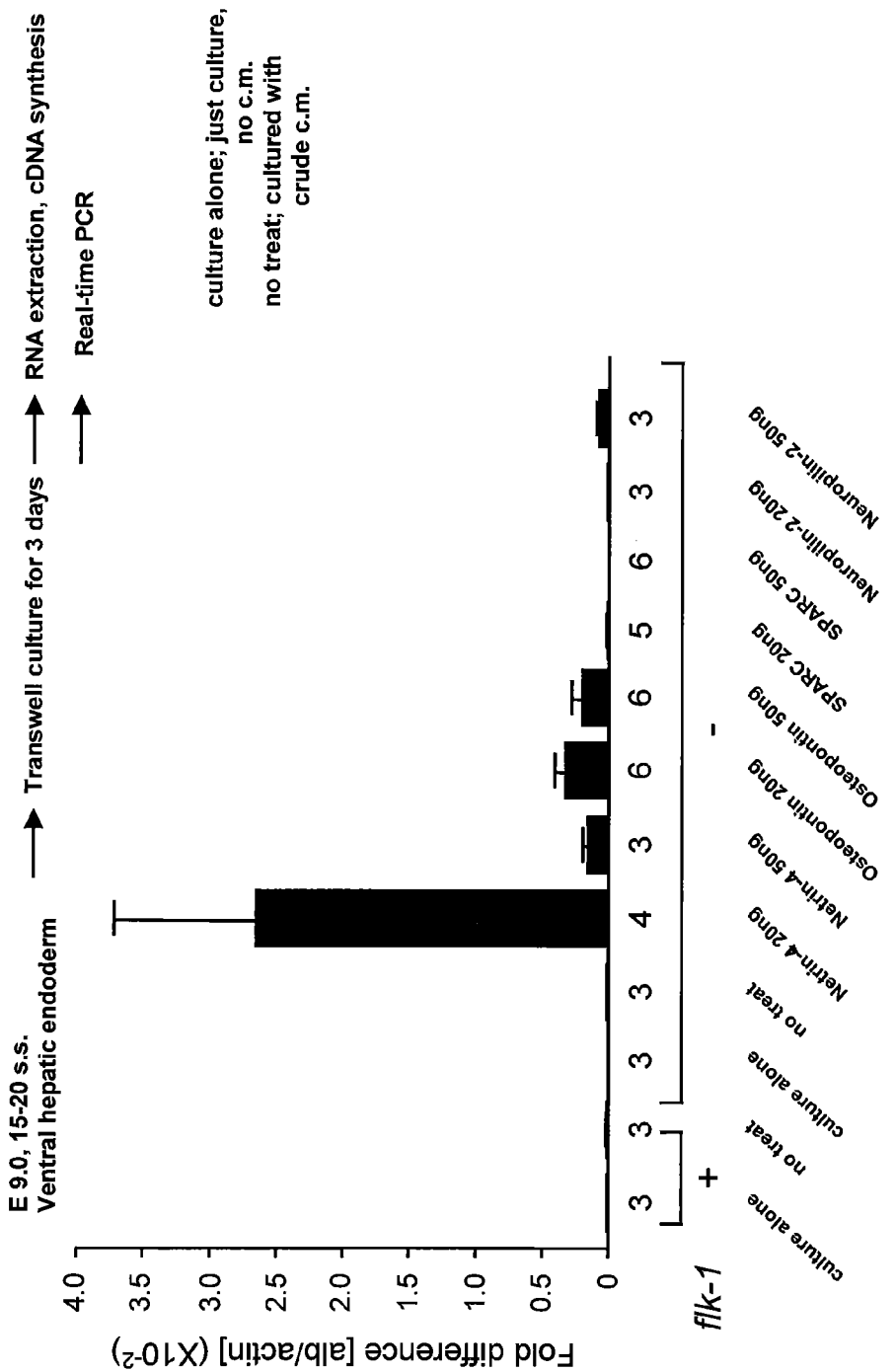
Figure 14B:
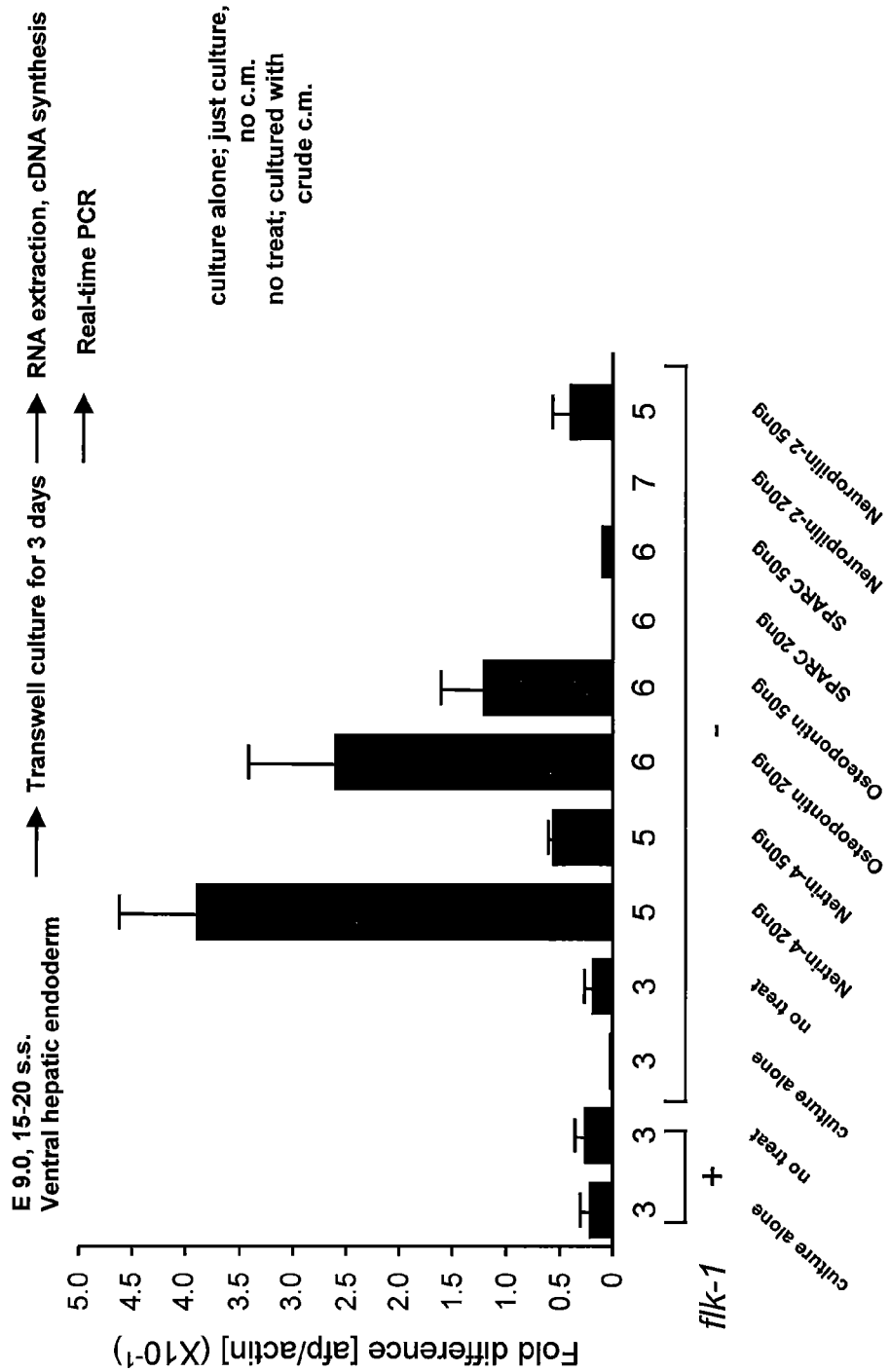
FIG. 14B depicts the effects of netrin-4 on alpha-fetoprotein.

In similar experiments, the effect of treatment with netrin-4 on induction of albumin and alpha-fetoprotein expression in liver bud explants from flk-1$^{-/-}$ embryos was examined (FIG. 14). It was found that netrin-4 treatment produced marked increases in the expression of these proteins (FIG. 14A, albumin; FIG. 14B, alpha-fetoprotein) in liver bud explants. These data show that netrin-4 treatment dramatically enhances liver differentiation of progenitor cells.

In particular embodiments, netrin-4 protein, netrin-4 mimetics, netrin-4 agonists, or compounds that modulate the activity of netrin-4 protein are used to induce the differentiation of endodermal cells, cells derived from embryonic stem cells, other stem and progenitor cells, and liver and pancreatic progenitor cells into pancreatic cells or liver cells, restore function to damaged pancreatic or liver tissue, or to treat diseases of those organs and tissues. Netrin-4 protein, as used in the context of the present invention, is intended to include human netrin-4 as set forth in SEQ ID NO:1 (FIG. 11; Koch, et al. 2000. *J. Cell Biol.* 151:221-234), as well as homologs, variants or biologically active fragments of netrin-4. Exemplary homologs of netrin-4 include *Mus musculus* netrin-4 (see, e.g., GENBANK Accession No. NP_067295; Yin, et al. 2000 *Mech. Dev.* 96:115-119) and *Danio rerio* netrin-4 (see, e.g., GENBANK Accession No. NP_001032775). An example of a netrin-4 variant or fragment includes a human netrin-4 protein which lacks the signal peptide region (see, e.g., Zhang, et al. 2004. *Brain Res Mol Brain Res.* 130 (1-2): 68-80).

As is conventional in the art, endodermal cells are cells which differentiate into epithelial cells of the pancreas, gut endothelial cells, and hepatocytes. An endodermal cell of the present invention, also commonly referred to as an endodermal progenitor cell, can be obtained using any conventional method known in the art, or alternatively, an endodermal cell can be a endodermal cell line. Moreover, an endodermal cell of the invention can be isolated or be a cell of a tissue explant, i.e., tissue taken from the body and grown in an artificial medium.

Also of use in the instant method are pancreatic and liver progenitor cells as well as cells derived from embryonic stem cells, adult stem cells or other stem or progenitor cells. It is contemplated that such cells can be directly differentiated into pancreatic or liver cells via netrin-4 treatment, or alternatively be simultaneously or sequentially exposed to other epigenetic signals that mimic in vivo pancreatic or liver development. For example, when employing embryonic stem cells, said cells can first be contacted with serum, activin and retinoic acid to generate pancreatic endodermal cells (Shim, et al. (2007) *Diabetologia*, PMID: 17457565) and subsequently matured to pancreatic cells via netrin-4 treatment. See also the teachings of Schroeder, et al. ((2006) *Nat. Protoc.* 1(2): 495-507) for epigenetic signals which differentiate embryonic stem cells into endodermal cells. Similarly, treatment of embryonic stem cells with human activin A and a deleted variant of hepatocyte growth factor (dHGF) (Chen, et al. (2006) *Cell Transplant.* 15(10):865-71) in combination with netrin-4 can be used to induce differentiation of hepatocytes. The isolation of stem cells and progenitor cells is routinely practiced in the art and any conventional method can be employed to isolate such cells.

Endodermal cells, cells derived from embryonic stem cells, other stem and progenitor cells, and liver and pancreatic progenitor cells of the present invention can be characterized in the following manner: responsiveness to growth factors, specific gene expression, antigenic markers on the surface of such cells, and/or basic morphology. For example, extent of growth factor responsivity, e.g., the concentration range of growth factor to which they will respond to, the maximal and minimal responses, and to what other growth factors and conditions to which they might respond, can be used to characterize the subject endodermal cells. Furthermore, isolated endodermal cells can be identified by the presence or absence of particular markers. By way of illustration, an endodermal progenitor cell can be identified by the expression of markers such as FoxA2 (HNF3 beta).

An endodermal cell, cells derived from embryonic stem cells, other stem and progenitor cells, and liver and pancreatic progenitor cells of the invention (including partially differentiated cells) can be maintained in tissue culture in vitro or ex vivo. There are a number of suitable tissue culture media that exist for culturing tissue from animals. Some of these are complex and some are simple. While endodermal, cells derived from embryonic stem cells, other stem and progenitor cells, and liver and pancreatic progenitor cells can be grown in complex media, it will generally be preferred that the explants be maintained in a simple medium, such as Dulbecco's Minimal Essential Media (DMEM), in order to effect more precise control over the differentiation of the endodermal cell, cells derived from embryonic stem cells, other stem and progenitor cells, and liver and pancreatic progenitor cells into the desired cell. Moreover, when the endodermal cell, other stem and progenitor cells, and liver and pancreatic progenitor cells is of an explant, the explant can be maintained in the absence of sera for extended periods of time. In some embodiments, growth factors or other mitogenic agents are not included in the primary media for maintenance of cell cultures in vitro, but are used subsequently to cause proliferation of distinct populations of cells. Such agents are well-known to those skilled in the art and include, but are not limited to, hepatocyte growth factor (HGF), Epidermal Growth Factor (EGF), Fibroblast Growth Factors (FGF), Keratinocyte growth factor (KGF), and the like.

Endodermal cell, cells derived from embryonic stem cells, other stem and progenitor cells, and liver and pancreatic progenitor cells cultures can be maintained in any suitable culture vessel, such as a 12- or 24-well microplate, and can be maintained under typical culture conditions for cells isolated from the same animal, e.g., such as 37° C. in 5% $CO_2$. The cultures can be shaken for improved aeration, the speed of shaking being, for example, 12 rpm.

In other embodiments, endodermal cells and/or explants are cultured on feeder layers, e.g., layers of feeder cells which secrete inductive factors or polymeric layers containing inductive factors.

In another embodiment, the subject endodermal cells are implanted into one of a number of regeneration models used in the art, e.g., a host animal which has undergone partial pancreatectomy.

In accordance with the present invention, cultured endodermal cells or explants containing endodermal cells are contacted with an effective amount of a netrin-4 protein, netrin-4 mimetic, to netrin-4 agonists so that said endodermal cells differentiate into pancreatic cells (e.g., pancreatic ductal or acinar cells), hepatocytes or bile duct structures, or alternatively intestinal epithelial cells. Differentiation in the present context refers to a status of cells in which the cells develop specific morphological or functional properties. Cells may differentiate into a specific tissue or organ. On the other hand, undifferentiated cells are difficult to distinguish each other in a population of cells, since each cell does not have any or little specific morphological or functional properties.

Determination of whether an endodermal cell has differentiated into a pancreatic or liver cell can be achieved by the detection of markers specific to these cell types. In an illustrative embodiment, proteins of the hepatocyte nuclear factor (HNF) transcription factor family, e.g., HNF1-4, are known to be expressed in liver progenitors at various times during liver development. For example, the endodermal cell can express FoxA2 (HNF3beta) and early liver progenitors can express HNF proteins such as HNF1α, HNF2β, HNF3γ, and/or HNF4. The glucose transporter Glut2 is also a marker for both early pancreatic cells.

In another illustrative embodiment, homeodomain type transcription factors such as STF-1 (also known as IPF-1, IDX-1 or PDX) have been shown to mark different populations of the developing pancreas. Some LIM genes have also been shown to regulate insulin gene expression and would also be markers for protodifferentiated β-islet cells. Likewise, certain of the PAX genes, such as PAX6, are expressed during pancreas formation and can be used to characterize certain pancreatic endodermal cell populations. Other markers of pancreatic endodermal cells include the pancreas-specific transcription factor PTF-1, and hXBP-1 and the like. Moreover, certain of the HNF proteins are expressed during early pancreas development and can used as markers for pancreatic endodermal cells.

Endodermal cells giving rise to pancreatic cells may also express such markers as villin and/or tyrosine hydroxylase, as well as secrete such factors as insulin, glucagon and/or neuropeptide Y.

In other embodiments, differentiated pancreatic cells can be characterized by binding to lectin(s), e.g., to a plant lectin such as peanut agglutinin. In certain embodiments, the lectin is *Amaranthus caudatus* Lectin (ACL, ACA); *Bauhinia purpurea* Lectin (BPL, BPA); Concanavalin A (Con A); Succinylated Concanavalin A (Con A); *Datura stramonium* Lectin (DSL); *Erythrina cristagalli* Lectin (ECL, ECA); *Galanthus nivalis* Lectin (GNL); Lens culinaris Agglutinin (LCA); Isolectin-B4; *Lycopersicon esculentum* (Tomato) Lectin (LEL, TL); *Narcissus pseudonarcissus* Lectin (NPL, NPA, DL); Peanut Agglutinin (PNA); *Phaseolus vulgaris* Agglutinin (PHA); *Pisum sativum* (PSA); *Solanum tuberosum* (Potato) Lectin (STL, PL); Soybean Agglutinin (SBA); Wheat Germ Agglutinin (WGA); Succinylated Wheat Germ Agglutinin; and the like.

For instance, various components of the human pancreas can be marked by different lectins. DSL marks inter- and intralobular ducts. LCA appears to mark mesenchyme. ECL marks intralobular ducts without marking larger ducts. Succinylated-Wheat Germ Agglutinin marks a subset of main duct cells and is quite restricted compared to WGA.

Endodermal cells giving rise to hepatocytes express markers such as albumin, HNF-4α, α-fetoprotein, transthyretin, and CK-18. Moreover, hepatocytes can be identified based on the development of at least one property of the liver, including but not limited to, regulation of blood sugar; regulation of lipids; regulation of amino acids; production of heat; formation of bile; formation of cholesterol; metabolism of hormones, toxins, etc.; formation of heparin; and storage of vitamins such as vitamin A and D.

Having demonstrated that netrin-4 induces differentiation of endodermal cells into pancreatic cells, it is contemplated that netrin-4 protein, as well as netrin-4 mimetics, netrin-4 agonists, compounds that modulate the activity of netrin-4, or cells differentiated with netrin-4 to exhibit pancreatic or liver phenotypes can be used in the treatment of a variety of diseases or conditions. Generally, treatment involves altering pancreatic or liver cell function, improving pancreatic or liver cell function, or replacing damaged pancreatic cells or liver cells to prevent or treat diseases or conditions of the pancreas or liver In some embodiments, the invention contemplates the in vivo administration of netrin-4 protein or a netrin-4 agonist to subjects which have been transplanted with pancreatic tissue, as well as to subjects which have a need for improved pancreatic performance, especially of glucose-dependent insulin secretion. In other embodiments, the invention provides in vitro or ex vivo differentiation of endodermal cells into cells exhibiting a pancreatic phenotype for transplant into subjects which have a need for improved pancreatic performance, especially of glucose-dependent insulin secretion. Accordingly, particular embodiments embrace differentiation of endodermal cells into insulin-producing cells, and more desirably, glucose-responsive insulin-producing cells. In still other embodiments, subjects in need of improved liver function or performance are administered a netrin-4 protein or cells differentiated with netrin-4 to treat diseases or conditions of the liver.

It is contemplated that the cells differentiated in vitro or ex vivo for use in treatment of a subject can be either syngeneic, allogeneic or xenogeneic. Thus, in certain embodiments, small samples of pancreatic or liver tissue from a donor or self can be obtained without sacrificing or seriously injuring the donor. The endodermal cells (e.g., either isolated or as cells of the explant) are subsequently contacted with a netrin-4 protein and optionally amplified, and subsequently injected or implanted into a recipient subject, i.e., either self or a suitable recipient. When allogeneic or xenogeneic transplantation is conducted, rejection response may optionally obviated by any method known in the art such as administering immunosuppressive agent (e.g., azathiopurine, cyclophosphamide, etc.).

In accordance with the present invention, treatment involves administration of an effective amount of a netrin-4 protein or netrin-4-differentiated endodermal cell, cells derived from embryonic stem cells, other stem and progenitor cells, and liver and pancreatic progenitor cells to a subject in need of treatment thereby ameliorating or alleviating at least one sign or symptom of the disease or condition of the subject. Generally, when treatment involves the use of a netrin-4 protein or netrin-4 mimetics, netrin-4 agonists, compounds that modulate the activity of netrin-4, such molecules are formulated into a pharmaceutical composition containing the molecule in admixture with a pharmaceutically acceptable vehicle. For example, the molecule could be formulated in any pharmaceutically acceptable vehicle that would be compatible with the type of cells or tissue being contacted. Formulations of the present invention contemplated would include injectable solutions as well as suitable oral, dermal, intramuscular, or subcutaneous formulations. Contemplated as well are vectors appropriate for delivering nucleic acid encoding a netrin-4 protein to the tissue or cells to be targeted.

Pharmaceutical compositions can be prepared by methods and contain vehicles which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically acceptable vehicle, composition or carrier, such as a liquid or solid filler, diluent, excipient, or solvent encapsulating material, is involved in carrying or transporting the subject compound from one organ, or portion of the body, to another organ, or portion of the body. Each vehicle must be acceptable in the sense of being compatible with the other ingredients of the formulation and not injurious to the subject being treated.

Examples of materials which can serve as pharmaceutically acceptable vehicles include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Pharmaceutical compositions appropriately formulated for parenteral (for example, by intravenous, intraperitoneal, subcutaneous or intramuscular injection), topical (including buccal and sublingual), oral, intranasal, intravaginal, or rectal administration can be prepared according to standard methods.

The selected dosage level will depend upon a variety of factors including the activity of the particular molecule employed, the route of administration, the time of administration, the rate of excretion or metabolism of the particular agent being employed, the duration of the treatment, other drugs, compounds and/or materials used in combination with the particular agent employed, the age, sex, weight, condition, general health and prior medical history of the patient being treated, and like factors well known in the medical arts. In the case of the treatment of cells either in vitro or ex vivo, doses of netrin-4 would be expected to be in the range of nanograms/ml or micrograms/ml.

A physician or veterinarian having ordinary skill in the art can readily determine and prescribe the effective amount of the pharmaceutical composition required. For example, the physician or veterinarian could start doses of a molecule at levels lower than that required in order to achieve the desired therapeutic effect and gradually increase the dosage until the desired effect is achieved.

In embodiments embracing treatment with cells which have been differentiated using a netrin-4 protein, common methods of administering such cells to subjects, particularly human subjects, are well-known in the art. Such methods include injection or implantation of the cells into target sites in the subjects using, e.g., a delivery device which facilitates introduction of the cells into the subjects. Such delivery devices include tubes, e.g., catheters, for injecting cells and fluids into the body of a recipient subject. In certain embodiments, the tubes additionally have a needle, e.g., a syringe, through which the cells of the invention can be introduced into the subject at a desired location. The differentiated cells of the invention can be inserted into such a delivery device, e.g., a syringe, in different forms. For example, the cells can be suspended in a solution or embedded in a support matrix when contained in such a delivery device. As used herein, the term "solution" includes a pharmaceutically acceptable vehicle in which the cells of the invention remain viable. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like.

Support matrices in which the differentiated cells can be incorporated or embedded include matrices which are recipient-compatible and which degrade into products which are not harmful to the recipient. Natural and/or synthetic biodegradable matrices are examples of such matrices. Natural biodegradable matrices include plasma clots, e.g., derived from a mammal, and collagen matrices. Synthetic biodegradable matrices include synthetic polymers such as polyanhydrides, polyorthoesters, and polylactic acid. Other examples of synthetic polymers and methods of incorporating or embedding cells into these matrices are known in the art. See, e.g., U.S. Pat. Nos. 4,298,002 and 5,308,701. These matrices provide support and protection for the fragile differentiated cells in vivo and are, therefore, a desired form in which the differentiated cells are introduced into the recipient subjects.

The present invention also provides substantially pure differentiated cells which can be used therapeutically for treatment of various disorders associated with insufficient functioning of the pancreas or liver.

To illustrate, the subject differentiated cells can be used in the treatment or prophylaxis of a variety of pancreatic disorders, both exocrine and endocrine. For instance, the differentiated cells can be used to repair a partial pancreatectomy, e.g., excision of a portion of the pancreas. Likewise, such cell populations can be used to regenerate or replace pancreatic tissue loss due to, pancreatolysis, e.g., destruction of pancreatic tissue, such as pancreatitis, i.e., a condition due to autolysis of pancreatic tissue caused by escape of enzymes into the substance.

In an exemplary embodiment, the subject differentiated cells can be provided to patients suffering from any insulin-deficiency disorder such as diabetes. Diabetes is characterized by pancreatic islet destruction or dysfunction leading to loss of glucose control. Diabetes mellitus is a metabolic disorder defined by the presence of chronically elevated levels of blood glucose (hyperglycemia). Insulin-dependent (Type 1) diabetes mellitus (IDDM) results from an autoimmune-mediated destruction of the pancreatic β-cells with consequent loss of insulin production, which results in hyperglycemia. Type 1 diabetics require insulin replacement therapy to ensure survival. Non-insulin-dependent (Type 2) diabetes mellitus (NIDDM) is initially characterized by hyperglycemia in the presence of higher-than-normal levels of plasma insulin (hyperinsulinemia). In Type 2 diabetes, tissue processes which control carbohydrate metabolism are believed to have decreased sensitivity to insulin. Progression of the Type 2 diabetic state is associated with increasing concentrations of blood glucose, and coupled with a relative decrease in the rate of glucose-induced insulin secretion.

The primary aim of treatment in both forms of diabetes mellitus is the same, namely, the reduction of blood glucose levels to as near normal as possible. Treatment of Type 1 diabetes involves administration of replacement doses of insulin. In contrast, treatment of Type 2 diabetes frequently does not require administration of insulin. For example, initial therapy of Type 2 diabetes may be based on diet and lifestyle changes augmented by therapy with oral hypoglycemic agents such as sulfonylurea. Insulin therapy may be required, however, especially in the later stages of the disease, to produce control of hyperglycemia in an attempt to minimize complications of the disease, which may arise from islet exhaustion.

Tissue-engineering approaches have also been employed, wherein treatment has focused on transplanting healthy pancreatic islets, usually encapsulated in a membrane to avoid immune rejection. Three general approaches have been tested in animal models. In the first, a tubular membrane is coiled in a housing that contained islets. The membrane is connected to a polymer graph that in turn connects the device to blood vessels. By manipulation of the membrane permeability, so as to allow free diffusion of glucose and insulin back and forth through the membrane, yet block passage of antibodies and lymphocytes, normoglycemia was maintained in pancreatectomized animals treated with this device (Sullivan et al. (1991) *Science* 252:718).

In a second approach, hollow fibers containing islet cells were immobilized in the polysaccharide alginate. When the device was place intraperitoneally in diabetic animals, blood glucose levels were lowered and good tissue compatibility was observed (Lacey et al. (1991) *Science* 254:1782).

Finally, islets have been placed in microcapsules composed of alginate or polyacrylates. In some cases, animals treated with these microcapsules maintained normoglycemia for over two years (Lim et al. (1980) *Science* 210:908; O'Shea et al. (1984) *Biochim. Biochys. Acta.* 840:133; Sugamori et al. (1989) *Trans. Am. Soc. Artif Intern. Organs* 35:791; Levesque et al. (1992) *Endocrinology* 130:644; and Lim et al. (1992) *Transplantation* 53:1180). However, all of these transplantation strategies require a large, reliable source of donor islets.

Differentiation of cells in accordance with the present invention can be used for treatment of diabetes because endodermal cells can be differentiated into cells of pancreatic lineage, e.g., β-islet cells. Endodermal cells, cells derived from embryonic stem cells, other stem and progenitor cells, and liver and pancreatic progenitor cells can be cultured in vitro in the presence of netrin-4 and under conditions which can further induce these cells to differentiate into mature pancreatic cells, or they can undergo differentiation in vivo once introduced into a subject. Many methods for encapsulating cells are known in the art. For example, a source of β-islet cells producing insulin is encapsulated in implantable hollow fibers. Such fibers can be pre-spun and subsequently loaded with the β-islet cells (U.S. Pat. Nos. 4,892,538; 5,106, 627; Hoffman et al. (1990) *Expt. Neurobiol.* 110:39-44; Jaeger et al. (1990) *Prog. Brain Res.* 82:41-46; and Aebischer et al. (1991) *J. Biomech. Eng.* 113:178-183), or can be co-extruded with a polymer which acts to form a polymeric coat about the β-islet cells (U.S. Pat. Nos. 4,391,909; 4,353,888; Sugamori et al. (1989) *Trans. Am. Artif. Intern. Organs* 35:791-799; Sefton et al. (1987) *Biotechnol. Bioeng.* 29:1135-1143; and Aebischer et al. (1991) *Biomaterials* 12:50-55).

Moreover, in addition to providing a source of implantable cells, either in the form of the progenitor cell population or the differentiated progeny thereof, the subject cells can be used to produce cultures of pancreatic cells for production and purification of secreted factors. For instance, cultured cells can be provided as a source of insulin. Likewise, exocrine cultures can be provided as a source for pancreatin.

Likewise, it is contemplated that differentiation of cells in accordance with the present invention can be used for treatment of hepatic diseases, disorders or conditions including but not limited to: alcoholic liver disease, hepatitis (A, B, C, D, etc.), focal liver lesions, primary hepatocellular carcinoma, large cystic lesions of the liver, focal nodular hyperplasia granulomatous liver disease, hepatic granulomas, hemochromatosis such as hereditary hemochromatosis, iron overload syndromes, acute fatty liver, hyperemesis gravidarum, intercurrent liver disease during pregnancy, intrahepatic cholestasis, liver failure, fulminant hepatic failure, jaundice or asymptomatic hyperbilirubinemia, injury to hepatocytes, Crigler-Najjar syndrome, Wilson's disease, alpha-1-antitrypsin deficiency, Gilbert's syndrome, hyperbilirubinemia, nonalcoholic steatohepatitis, porphyrias, noncirrhotic portal hypertension, noncirrhotic portal hypertension, portal fibrosis, schistosomiasis, primary biliary cirrhosis, Budd-Chiari syndrome, hepatic veno-occlusive disease following bone marrow transplantation, etc.

Yet another aspect of the present invention provides methods for screening various compounds for their ability to modulate growth, proliferation or differentiation of distinct endodermal cell populations. In an illustrative embodiment, the subject endodermal cells, and their differentiated progeny, can be used to screen various compounds or natural products. Such cells can be maintained in minimal culture media for extended periods of time (e.g., for 7-21 days or longer) and can be contacted with any compound, e.g., small molecule or natural product, e.g., growth factor, to determine the effect of such compound on cellular growth, proliferation or differentiation of the endodermal cells. Detection and quantification of growth, proliferation or differentiation of these cells in response to a given compound provides a means for determining the compound's efficacy at inducing one of the growth, proliferation or differentiation in a given cell type. Methods of measuring cell proliferation are well-known in the art and most commonly include determining DNA synthesis characteristic of cell replication. There are numerous methods in the art for measuring DNA synthesis, any of which may be used according to the invention. In an embodiment of the invention, DNA synthesis can be determined using a radioactive label ($^3$H-thymidine) or labeled nucleotide analogues (BrdU) for detection by immunofluorescence. The efficacy of the compound can be assessed by generating dose response curves from data obtained using various concentrations of the compound. A control assay can also be performed to provide a baseline for comparison. Identification of the endodermal cell population(s) amplified in response to a given test agent can be carried out according to such phenotyping as described above.

The following non-limiting examples are provided to further illustrate the present invention.

EXAMPLES

Example 1

Liver and Pancreatic Endoderm Dissection and Transwell Culture

The purpose of this explant system is to support the morphogenetic changes of liver or pancreatic bud into highly differentiated structure. This system allows tissue to grow 3-dimensionally, and allows for examination of morphological changes of specific cell domains in vitro, rather than only detection of the expression of specific genes in explants.

a) Preparation

Culture medium was prepared. Dulbecco's modified Eagle medium containing 10% calf serum (Hyclone), penicillin (100 unit/ml)/streptomycin (100 g/ml) was used as culture media, also containing 0.2% Matrigel (Collaborative Biomedical Products, Becton Dickinson). Transwell culture plates (Corning; 12 mm membrane diameter and 3.0 micrometer pore size) were used. The upper chambers of the plates were coated with 400 microliters of collagen substrata containing 96.3 microgram/ml of Collagen Type 1 (BD Biosciences) in 0.02 N acetic acid/phosphate-buffered saline (PBS) at 37° C. for at least for 1 hour. Then the solution was aspirated and the upper chambers were washed twice with pre-warmed PBS and once with medium. Just before starting tissue culture, the medium was aspirated from the upper chamber and 400 microliters/well of culture medium with 0.2% matrigel was replaces in the upper chambers, with 600 microliters/well of the same medium being places in the lower chambers.

b) Dissection of Foregut Endoderm

Liver and dorsal pancreatic bud region can be recognized morphologically after E9.0. For the studies of morphological changes in liver and dorsal pancreatic bud, embryos from E9.0-10.0 were used and cultured onto the Transwell plates as described above.

Noon of the day of vaginal plug discovery was identified as E0.5. Embryos were removed from uteri at appropriate times, transferred to dishes containing PBS and 0.1% BSA, and dissected free from decidual tissues. The embryos were then transferred to black wax dissecting dishes containing a few drops of PBS with 0.1% BSA.

The yolk sac was then carefully removed under a dissecting microscope, using electrolytically etched tangusten needles. The cardiac tube and midgut/hindgut below the liver and dorsal pancreatic bud were then removed, so that the midsection could be obtained. By changing the direction of the midsection, the gut tube was recognized. The liver and dorsal pancreatic bud regions were then cut from the gut tube. After cleaning away extra tissue, the explants were transferred to the upper chambers of the Transwell plates.

c) Tissue Culture

The explants were incubated in 5% $CO_2$/95% air at 37° C. for 1-3 days and subjected to further experiments. Under a microscope, the presence of cardiac mesodermal cells in the explants were recognized as beating cells. The growth of explants were recorded with a phase contrast microscope.

After culturing, the explants were subjected to RNA extraction for RT-PCR (real-time PCR), in situ hybridization, or immunohistochemistry. For in situ hybridization and immunohistochemistry, tissues were fixed on the slide in 4% paraformaldehyde in PBS for a few hours to overnight at 4° C., then dehydrated with a series of methanol washes. The explants were stored at −20° C. for several months.

What is claimed is:

1. A method for promoting differentiation of a partially differentiated pancreatic progenitor cell comprising contacting a partially differentiated pancreatic progenitor cell with an effective amount of netrin-4, thereby promoting differentiation of said pancreatic progenitor cell into a pancreatic cell which expresses Ptf1a$^{p48}$ and Ngn-3.

2. A method for promoting differentiation of a partially differentiated liver progenitor cell comprising contacting a partially differentiated liver progenitor cell with an effective amount of netrin-4, thereby promoting differentiation of said liver progenitor cell into a liver cell which expresses albumin and alpha-fetoprotein.

* * * * *